US012746190B2

(12) United States Patent
Zhao

(10) Patent No.: US 12,746,190 B2
(45) Date of Patent: Sep. 29, 2026

(54) SOLID COMPOSITION IN THE FORM OF WATER-IN-OIL EMULSION

(71) Applicant: L'OREAL, Paris (FR)

(72) Inventor: Yujie Zhao, Shanghai (CN)

(73) Assignee: L'OREAL, Paris (FR)

( * ) Notice: Subject to any disclaimer, the term of this patent is extended or adjusted under 35 U.S.C. 154(b) by 589 days.

(21) Appl. No.: 17/785,701

(22) PCT Filed: Dec. 19, 2019

(86) PCT No.: PCT/CN2019/126522
§ 371 (c)(1),
(2) Date: Jun. 15, 2022

(87) PCT Pub. No.: WO2021/120084
PCT Pub. Date: Jun. 24, 2021

(65) Prior Publication Data

US 2023/0070172 A1 Mar. 9, 2023

(51) Int. Cl.

| | |
|---|---|
| ***A61K 8/06*** | (2006.01) |
| ***A61K 8/81*** | (2006.01) |
| ***A61K 8/891*** | (2006.01) |
| ***A61K 8/92*** | (2006.01) |
| ***A61Q 1/02*** | (2006.01) |

(52) U.S. Cl.
CPC ............ *A61K 8/064* (2013.01); *A61K 8/8111* (2013.01); *A61K 8/891* (2013.01); *A61K 8/922* (2013.01); *A61Q 1/02* (2013.01)

(58) Field of Classification Search
CPC ........................................................ A61K 8/064
See application file for complete search history.

(56) References Cited

U.S. PATENT DOCUMENTS

| | | | | |
|---|---|---|---|---|
| 4,606,914 A * | 8/1986 | Miyoshi | A61Q 1/10 514/789 |
| 7,083,800 B1 * | 8/2006 | Terren | A61K 8/8111 424/59 |
| 7,776,348 B2 | 8/2010 | Gardel et al. | |
| 7,842,725 B2 * | 11/2010 | Wegner | A01N 25/16 424/404 |
| 2006/0083696 A1 | 4/2006 | Yu et al. | |
| 2008/0138300 A2 | 6/2008 | Yu et al. | |
| 2016/0008263 A1 | 1/2016 | Mendoza | |
| 2019/0388306 A1 | 12/2019 | Ravni et al. | |

FOREIGN PATENT DOCUMENTS

| | | | |
|---|---|---|---|
| CN | 1471903 A | 2/2004 | |
| CN | 110225741 A | 9/2019 | |
| EP | 1 647 268 A1 | 4/2006 | |
| FR | 2 911 496 A1 | 7/2008 | |
| FR | 2 939 033 A1 | 6/2010 | |
| KR | 20180011091 A * | 1/2018 | A61K 8/31 |
| KR | 10-2019-0109434 | 9/2019 | |
| WO | WO 2016/007519 A1 | 1/2016 | |
| WO | WO 2018/113986 A1 | 6/2018 | |
| WO | WO-2018115328 A1 * | 6/2018 | A61K 8/0229 |
| WO | WO 2018/142076 A1 | 8/2018 | |

OTHER PUBLICATIONS

Machine translation of Ravni, et al., KR20190109434A [online]. Espacenet [retrieved on Oct. 30, 2024]. Retrieved from the internet: <https://worldwide.espacenet.com/patent/>. (Year: 2019).*
GSRS—Hydrogenated Jojoba Oil, Randomized, (online), [retrieved on Nov. 12, 2024], retrieved online <https://gsrs.ncats.nih.gov/ginas/app/ui/substances/33dd944a-63cd-451b-95ba-4990d7eec59a>. (Year: 2024).*
Office Action issued on Jun. 19, 2023 in the Japanese Patent Application No. 2022-521451, 3 pages.
Combined Chinese Office Action and Search Report issued Apr. 1, 2023 in Chinese Patent Application No. 201980103072.X, 7 pages.
International Search Report issued Sep. 24, 2020 in PCT/CN2019/126522, filed on Dec. 19, 2019, 6 pages.
Written Opinion issued Sep. 24, 2020 in PCT/CN2019/126522, filed on Dec. 19, 2019, 6 pages.
Combined Russian Office Action and Search Report issued Feb. 10, 2023 in Russian Patent Application No. 2022116381/04 (with English Translation of Office Action only), 12 pages.
Tada et al., "Analysis of the Constituents in Jojoba Wax Used as a Food Additive by LC/MS/MS." Journal of the Food Hygienic Society of Japan, vol. 46, No. 5, Oct. 2005, pp. 198-204 (total 7 pages).
Extended European Search Report issued Aug. 11, 2023, in corresponding European Patent Application No. 19956946.8, 7 pages.
Database GNPD [Online] Mintel; May 9, 2017, anonymous: "Radiant Stick Foundation", XP093070323, Database accession No. 4793487, pp. 1-8.
Office Action issued Nov. 20, 2023, in corresponding Japanese Patent Application No. 2022-521451, 2 pages.
Korean Office Action issued Jun. 12, 2024 in Korean Patent Application No. 10-2022-7009877 (with English translation), 15 pages.
European Office Action issued Apr. 3, 2025 in European Patent Application No. 19956946.8, 5 pages.

* cited by examiner

*Primary Examiner* — Gina C Justice
(74) *Attorney, Agent, or Firm* — Oblon, McClelland, Maier & Neustadt, L.L.P.

(57) ABSTRACT

It relates to a solid composition in form of a water-in-oil emulsion comprising: (i) at least one silicone oil; (ii) at least two waxes having a melting point of greater than or equal to 65° C. including polyethylene wax and jojoba ester wax; (iii) at least 5 wt. % of pigment, relative to the total weight of the composition; and (iv) no less than 40 wt. % of an aqueous phase, relative to the total weight of the composition. It also relates to a cosmetic method for caring for and/or making up the skin.

14 Claims, No Drawings

SOLID COMPOSITION IN THE FORM OF WATER-IN-OIL EMULSION

TECHNICAL FIELD

The present invention relates to a composition for making up and/or caring for the skin. Particularly, the present invention relates to a solid composition in the form of water-in-oil emulsion. The present invention also relates to a cosmetic method for making up and/or caring for the skin.

BACKGROUND ART

Foundation compositions are commonly used to contribute to an attractive color of the skin, in particular the face, and/or conceal imperfections of the skin, such as red blotches or blemishes. Conventional foundations exist in fluid or solid form, and each possesses its own advantages due to its form.

WO 2012/145862 discloses fluid foundation compositions in the form of a water-in-silicone emulsion, comprising a fatty phase, an aqueous phase and at least one organopolysiloxane elastomer, at least one dimethicone copolyol, and at least one $C_8$-$C_{22}$ alkyl dimethicone. The fatty phase comprises at least one volatile oil and/or at least one nonvolatile oil and optionally at least one wax.

However, the foundations of the prior art, due to their fluid form, are found not easy to carry with and apply on the skin.

In general, consumers are attracted by a cosmetic composition, especially a foundation, which is easy to use, provides good makeup finish and brings a good sensory.

By "easy to use" we intend to mean the composition is easy to carry with and to apply on the skin.

By "good makeup finish" we intend to mean the composition has good spreadability.

By "good sensory" we intend to mean a fresh and watery sensation.

Efforts have been made to develop compositions with these properties.

Besides, the stability is still to be improved.

Therefore, there is a need for developing solid compositions which are easy to carry with and to apply on the skin, with the fingers or an applicator by the users.

There is also a need for developing a solid composition having good spreadability when applied on the skin and more particularly on the face and/or neck.

There is also a need for developing a solid composition that, when applied on the skin and more particularly on the face and/or neck, providing a good sensory, i.e., fresh and watery sensation, while presenting a good stability over time and temperature variations.

SUMMARY OF THE INVENTION

The present invention aims to provide a solid composition, which is easy to carry with and to apply on the skin, has a good stability over time and temperature variations, and having good spreadability and providing good sensory when applied on the skin.

Thus, according to a first aspect, the present invention provides a solid composition in the form of a water-in-oil emulsion comprising:

(i) at least one silicone oil;

(ii) at least two waxes having a melting point of greater than or equal to 65° C. including polyethylene wax and jojoba ester wax;

(iii) at least 5 wt. % of pigment, relative to the total weight of the composition; and (iv) no less than 40 wt. % of an aqueous phase, relative to the total weight of the composition.

Surprisingly, the inventors have discovered that the composition according to the present invention is easy to carry with and to apply on the skin, has a good stability over time and temperature variations, and has good spreadability and provides good sensory when applied on the skin.

More surprisingly, it has been observed that, the combination of at least two waxes having a melting point of greater than or equal to 65° C. including polyethylene wax and jojoba ester wax, silicone oil and no less than 40 wt. % of aqueous phase provides a good balance of sensory, spreadability and stability.

According to a second aspect, the present invention provides a cosmetic method for caring for and/or making up the skin, comprising application of a composition of the present invention on the skin.

Other subjects and characteristics, aspects and advantages of the present invention will emerge even more clearly on reading the description and the examples that follows.

DETAILED DESCRIPTION OF THE INVENTION

According to the first aspect, the present invention provides a solid composition in the form of a water-in-oil emulsion comprising:

(i) at least one silicone oil;

(ii) at least two wax having a melting point of greater than or equal to 65° C. including polyethylene wax and jojoba ester wax; and (iii) at least 5 wt. % of pigment, relative to the total weight of the composition;

(iv) no less than 40 wt. % of an aqueous phase, relative to the total weight of the composition.

In that which follows and unless otherwise indicated, the limits of a range of values are included within this range, in particular in the expressions "of between" and "from . . . to . . . ".

For the purposes of the present invention, the term "skin" is intended to mean human skin and cover the face, the neck and the lips.

Moreover, the expression "at least one" used in the present description is equivalent to the expression "one or more".

Throughout the instant application, the term "comprising" is to be interpreted as encompassing all specifically mentioned features as well optional, additional, unspecified ones.

As used herein, the use of the term "comprising" also discloses the embodiment wherein no features other than the specifically mentioned features are present (i.e. "consisting of").

For the purpose of the present invention, "stable" refers to a composition which, after having been placed in an oven at 45° C., 37° C., and 4° C. for two months, does not, when returned to ambient temperature, exhibit grains perceptible to the touch when a fine layer of the composition is sheared between the fingers.

The composition according to the present invention is a foundation preferably under the form of compact emulsion or cast solid products, for example, a stick foundation.

For the purpose of the present invention, the term "solid" means the composition does not flow under its own weight at room temperature (25° C.).

The solid nature of the compositions can be determined by determining the hardness of the compositions. The hardness of a composition may, for example, be expressed by force in gram (g). Solid compositions of the present invention may, for example, have a hardness ranging from 20 g to 200 g, such as from 20 g to 90 g, from 20 g to 80 g and further such as from 20 g to 60 g, from 20 g to 40 g.

The hardness of a solid composition is measured according to the following protocol.

The composition the hardness of which is to be determined is stored at 20° C. for 24 hours before measuring the hardness.

This hardness is measured according to a method of penetrating a probe into the composition and in particular using a texture analyzer (for example TA-XT PLUS from Stable Micro System) equipped with a probe with a diameter of 3.26 mm. The hardness measurement is carried out at 20° C. at the center of 5 samples of the composition. The cylinder is introduced into each sample of composition at a pre-speed of 1.5 mm/s and then at a speed of 2 mm/s and finally at a post-speed of 10 mm/s, the total displacement being 5 mm. The recorded hardness value is that of the maximum peak observed.

For a measurement at a different temperature, the stick is stored for 24 hours at this new temperature before the measurement.

Silicone Oil

According to the first aspect, the composition of the present invention comprises at least one silicone oil.

The term "silicone oil" means an oil comprising at least one silicon atom, and especially comprising Si—O groups. The silicone oil(s) may be volatile or non-volatile.

As used herein, by "oils" or "oil" it means compounds having a melting point of less than about 30° C. and generally insoluble in water and including a hydrophobic moiety. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

The term "volatile" refers to a compound that can evaporate on contact with the skin in less than one hour, at room temperature and atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13,000 Pa (0.01 to 100 mmHg) and preferentially ranging from 1.3 Pa to 1300 Pa (0.01 to 10 mmHg).

In certain embodiments, the volatile silicone oils that may be mentioned include cyclopolydimethylsiloxanes (INCI name: cyclomethicone), such as cyclopentasiloxane, cyclohexasiloxane, octylmethylcyclotetrasiloxane, decamethylcyclopentasiloxane, dodecamethylcyclohexasiloxane; linear silicones such as heptamethylhexyltrisiloxane, heptamethyloctyltrisiloxane, hexamethyldisiloxane, octamethyltrisiloxane, decamethyltetrasiloxane and dodecamethylpentasiloxane.

In certain embodiments, the silicone oil may be selected from linear or cyclic silicone oils, such as linear or cyclic polydimethylsiloxanes (PDMSs), which are liquid or pasty at room temperature, especially cyclopolydimethylsiloxanes (cyclomethicones) such as cyclohexasiloxane; polymethylsiloxanes comprising alkyl, alkoxy or phenyl groups, which are pendent or at the end of a silicone chain, these groups containing from 2 to 24 carbon atoms, phenyl silicones, for instance phenyl trimethicones, phenyl dimethicones, phenyltrimethylsiloxydiphenyl-siloxanes, diphenyl dimethicones, diphenylmethyl-diphenyltrisiloxanes or 2-phenylethyl trimethylsiloxy silicates, and polymethylphenylsiloxanes, combinations thereof.

Preferably, the silicone oil is selected from polydimethylsiloxane.

Advantageously, the silicone oil is present in an amount ranging from 20 wt. % to 45 wt. %, preferably from 20 wt. % to 40 wt. %, more preferably from 25 wt. % to 35 wt. %, relative to the total amount of the composition.

Waxes

According to the first aspect, the composition of the present invention comprises at least two waxes having a melting point of greater than or equal to 65° C. including polyethylene wax and jojoba ester wax and at least one solid fatty substance.

The wax under consideration in the context of the present invention is generally a lipophilic compound that is solid at room temperature (25° C.), with a solid/liquid reversible change of state.

According to the present invention, the composition comprises a combination of polyethylene wax and jojoba ester wax, both of them having a melting point of greater than or equal to 65° C.

Polyethylene Wax

The polyethylene wax with a melting point of greater than or equal to 65° C. used according to the invention is an ethylene homopolymer or a copolymer of ethylene and of another copolymerizable monomer corresponding to the following formula (I):

$$CH_2{=}CHR \quad (I)$$

wherein

R represents a linear or branched alkyl chain which can be interrupted by mono- or polyoxyalkylene units, an aryl or aralkyl radical or $-CH_2COOH$ or $-CH_2CH_2OH$ radical.

The alkyl radicals more particularly denote the methyl, ethyl, propyl, isopropyl, decyl, dodecyl and octadecyl radicals.

The mono- or polyoxyalkylene units preferably denote mono- or polyoxyethylene groups or mono- or polyoxypropylene groups.

The aryl radical is preferably a phenyl or tolyl radical.

The aralkyl radical is, for example, a benzyl or phenethyl radical.

The weight-average molar mass of the polyethylene wax with a high melting point according to the invention is preferably between approximately 400 and 1000, more particularly between approximately 400 and 700 and is preferably about 500.

According to a preferred embodiment, the wax as defined above is selected from ethylene homopolymers, copolymers of ethylene and of propylene, copolymers of ethylene and of maleic anhydride or acid, or oxidized or ethoxylated polyethylenes.

Mention may in particular be made, among the ethylene homopolymers which can be used according to the invention, of those sold under the names of Polywax 500, Polywax 655 and Polywax 1000 by the company Petrolite.

Mention may be made, among the ethylene copolymers which can be used according to the invention, of the copolymers of ethylene and of propylene sold under the names Petrolite® by the company Petrolite, the copolymers of ethylene and of maleic anhydride sold under the names Ceramer® by the company Petrolite, the oxidized polyethylenes sold under the names Unilin® and Unicid® by the company Petrolite, and the ethoxylated polyethylenes sold under the names Unithox® by the company Petrolite.

According to a particularly preferred embodiment of the invention, the polyethylene wax is an ethylene homopolymer wax. Mentions may be made of polyethylene which, for example, is sold under the tradename Performalene 500-L Polyethylene by the company New Phase Technologies.

Preferably, the polyethylene wax is present in an amount ranging from ranging from 2 wt. % to 10 wt. %, preferably from 2 wt. % to 8 wt. %, more preferably from 2 wt. % to 5 wt. %, relative to the total amount of the composition.

Jojoba Ester Wax

Jojoba ester wax with a melting point of greater than or equal to 65° C. used according to the invention can be saturated form of jojoba esters, which can be fully hydrogenated jojoba ester of formula (II):

$$R^1—COO—CH_2—R^1 \qquad (II)$$

wherein $R^1$ comprises $CH_3—(CH_2)_y—$, y is 16, 18, 20 or 22.

The jojoba ester wax can be obtained by hydrogenation of jojoba wax ester (jojoba oil) of the following formula:

$$CH_3—(CH_2)_7—CH{=}CH—CH_2—(CH_2)_x—\overset{\overset{\large O}{\|}}{C}—O—CH_2—(CH_2)_Y—CH_2—CH{=}CH—(CH_2)_7—CH_3$$

wherein x and y are 6, 8, 10 or 12.

The jojoba wax esters are composed of straight chain monounsaturated fatty alcohols and monounsaturated fatty acids. The single double bond is located in the middle (n−9 position), counting from the terminal methyl group, ($—CH_3$) of respective fatty acid or alcohol chain. Such wax esters are composed of fatty alcohols and fatty acids of even number of carbon atoms, primarily 20 and 22 carbons. The resulting esters have chain lengths of 38, 40, 42 and 44 with a small amount of esters of 36- and 4-carbon atoms being present. The typical composition of the wax esters is set out below.

| Wax esters | | |
|---|---|---|
| (X, Y) | Wax Ester Chain Length | Typical % (area by GC) |
| (6, 6) | 36 | 1 |
| (6, 8) (8, 6) | 38 | 8 |
| (6, 10) (8, 8) (10, 6) | 40 | 39 |
| (10, 8) (8, 10) | 42 | 38 |
| (10, 10) | 44 | 13 |
| (12, 10) (10, 12) | 46 | 1 |

The jojoba wax ester can be derived from the seed of the jojoba plant (*Simmondsia chinensis*).

As examples of Jojoba ester wax with a melting point of greater than or equal to 65° C., mention can be made to Floraesters® 70 sold by International Flora Technologies Ltd; Jojoba Esters-70 sold by the company vantage.

Preferably, the jojoba ester wax is present in an amount ranging from ranging from 1 wt. % to 10 wt. %, preferably from 1.5 wt. % to 8 wt. %, more preferably from 2 wt. % to 5 wt. %, relative to the total amount of the composition.

Additional Wax

In addition to polyethylene wax and jojoba ester wax mentioned above, the composition according to the present invention can comprise an additional wax.

As illustrations of waxes that are suitable for the present invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, microcrystalline waxes, paraffins, and ozokerite; the waxes obtained by Fischer-Tropsch synthesis and waxy copolymers, and also esters thereof, fatty acids or esters obtained by catalytic hydrogenation of animal or plant oils containing linear or branched $C_8$-$C_{32}$ fatty chains, preferably $C_{16}$ to $C_{18}$ chains, silicone waxes and fluoro waxes, or a mixture thereof.

Mention may also be made of fatty acids obtained by catalytic hydrogenation of animal or plant oils containing linear or branched $C_8$-$C_{32}$ fatty chains, preferably $C_{16}$ to $C_{18}$ chains. Among these compounds, mention may be made especially of stearic acid, palmitic acid, or a mixture thereof. The fatty acids used in the present invention are commercially available under the trade names, for example, AEC Stearic Acid sold by A & E Connock (Perfumery & Cosmetics) Ltd., Emersol sold by Emery Oleochemical LLC, Palmitic Acid PC sold by Protameen Chemicals, Inc.

As for esters obtained by catalytic hydrogenation of animal or plant oils, mention may be made to the waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

The waxes obtained by hydrogenation of olive oil esterified with $C_{12}$ to $C_{18}$ chain fatty alcohols such as those sold by the company SOPHIM under the brand names Phytowax Olive 12L44, 14L48, 16L55 and 18L57, are also convenient.

A wax that may be used is a $C_{20}$-$C_{40}$ alkyl (hydroxystearyloxy) stearate (the alkyl group containing from 20 to 40 carbon atoms), alone or as a mixture. Such a wax is especially sold under the names Kester Wax K 82 P®, Hydroxypolyester K 82 P® and Kester Wax K 80 P® by the company Koster Keunen.

Mentions may be made of candelilla (*Euphorbia cerifera* wax), such as the one sold under the reference "NC 1630" sold by Cera Rica Noda, Mentions may also be made of ozokerite, such as the commercial reference "Ozokerite Wax SP 1020 P" sold by Strahl & Pitsch, If presents, the additional waxes can be present in an amount ranging from 0.1% to 10% by weight, preferably of 0.5% to 5% by weight and especially of 1% to 4% by weight, relative to the total weight of the composition.

Pigments

According to the first aspect, the composition of the present invention comprises at least 5.0 wt. % of pigment, relative to the total weight of the composition.

"Pigments" are white or coloured, organic or inorganic, hydrophilic or hydrophobic, non-interference particles which are insoluble in aqueous and non-aqueous media and are intended for colouring the composition.

Inorganic pigments can be used in the present invention include oxides or dioxides of titanium, zirconium or cerium, and also oxides of zinc, iron or chromium, mica, Prussian blue, manganese violet, ultramarine blue and chromium hydrate, and mixtures thereof.

The organic pigments can be used in the present invention include D & C pigments, lakes based on cochineal carmine, and on barium, strontium, calcium and aluminium, or else the diketopyrrolopyrroles (DPP) which are described in documents EP-A-542 669, EP-A-787 730, EP-A-787 731 and WO-A-96/08537.

Advantageously, the pigments can be used in the present invention is a hydrophobic pigment, treated or untreated.

Use will be made of inorganic pigments, selected more particularly from titanium oxides and iron oxides (especially yellow, black and red), mica, untreated or treated with at least one hydrophobic agent.

The pigments can be used in the present invention are preferably wholly or partly surface-treated with a hydrophobic agent, more particularly with a fluoro, fatty acid or amino acid, or silicone compound, or a mixture thereof.

By way of example, the hydrophobic treatment agent may be selected from fatty acids such as stearic acid; metal soaps such as aluminium dimyristate and the aluminium salt of hydrogenated tallow glutamate; perfluoroalkyl phosphates and polyhexafluoropropylene oxides; perfluoropolyethers; amino acids; N-acylamino acids or salts thereof; lecithin, isopropyl triisostearyl titanate, isostearyl sebacate, and silicone compounds such as dimethicones or polydimethylsiloxanes, and mixtures thereof.

The hydrophobic treatment agent is preferably selected from perfluoroalkyl phosphates, polyhexafluoropropylene oxides, perfluoropolyethers, amino acids, N-acylamino acids or salts thereof, isopropyl triisostearyl titanate, and mixtures thereof.

More preferably, the hydrophobic agent is selected from perfluoroalkyl phosphates, N-acylamino acids or salts thereof, isopropyl triisostearyl titanate, and mixtures thereof.

The surface-treated pigments may be prepared according to chemical, electronic, chemomechanical or mechanical surface treatment techniques that are well known to the skilled person. It is also possible to use commercial products.

The surface agent may be absorbed or adsorbed on the pigments by solvent evaporation, chemical reaction and creation of a covalent bond.

According to one version, the surface treatment comprises a coating of the pigments.

The coating may represent from 0.1 to 10% by weight and more particularly from 1% to 5% by weight, of the total weight of the coated pigments.

Coating may be carried out, for example, by adsorption of a liquid surface agent on the surface of the pigments, by simple mixing with stirring of the pigments and of said surface agent, optionally under hot conditions, prior to the incorporation of the pigments into the other ingredients of the care or makeup composition.

Coating may be carried out, for example, by chemical reaction of a surface agent with the surface of the pigments and creation of a covalent bond between the surface agent and the pigments. This method is described especially in U.S. Pat. No. 4,578,266.

The hydrophobic treatment agent may be selected from fatty acids, such as stearic acid; metal soaps, such as aluminium dimyristate and the aluminium salt of hydrogenated tallow glutamate; amino acids; N-acylamino acids or salts thereof; lecithin, isopropyl trisostearyltitanate (or alternatively called ITT), and mixtures thereof.

The N-acylamino acids may comprise an acyl group having from 8 to 22 carbon atoms, such as, for example, a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine.

The fatty acids in the present invention are more particularly acids with hydrocarbon chains having from 1 to 30 carbon atoms, preferably having from 5 to 18 carbon atoms. The hydrocarbon chain may be saturated, monounsaturated or polyunsaturated.

Examples of pigments coated with fatty acids include those containing the disodium stearoylglutamate/aluminium hydroxide pairing, these being sold in particular under the trade name NAI-TAO-77891, NAI-C33-8073-10, NAI-C33-8075, NAI-C47-051-10, NAI-C33-115, NAI-C33-134, NAI-C33-8001-10, NAI-C33-7001-10, NAI-C33-9001-10 from the company Miyoshi Kasei.

Examples of pigments treated with isopropyltitanium triisostearate (ITT) include those sold under the trade name BWBO-12 (Iron oxide CI77499 and isopropyl titanium triisostearate), BWYO-12 (Iron oxide CI77492 and isopropyl titanium triisostearate) and BWRO-12 (Iron oxide CI77491 and isopropyl titanium triisostearate) by the company Kobo.

Preferably, pigments coated with fatty acids, such as those containing disodium stearoylglutamate/aluminium hydroxide pairing are used in the present invention.

Preferably, the pigment of the present invention is selected from mica, titanium oxides and iron oxides, untreated or coated with the disodium stearoylglutamate/aluminium hydroxide pairing, or a mixture thereof.

Advantageously, the pigment is present in an amount up to 18 wt. %, relative to the total weight of the composition.

Aqueous Phase

The composition according to the present invention comprises an aqueous phase.

The aqueous phase is present in an amount equal or above 40% by weight, in particular from 40% to 50%, especially between 40% and 45% by weight, relative to the total weight of the composition.

In one embodiment, this aqueous phase can comprise alcohol(s), in particular polyethylene glycols having from 6 to 80 ethylene oxide units; polyols, such as propylene glycol, isoprene glycol, butylene glycol, pentylene glycol, glycerin, maltitol, sorbitol, dipropylene glycol or diethylene glycol, glycol ethers, such as mono-, di- or tripropylene glycol or mono-, di- or triethylene glycol ($C_1$-$C_4$) alkyl ether, and any mixture thereof.

In one preferred embodiment, the aqueous phase of the present invention comprises at least one polyol. Preferably, the polyol is selected from propylene glycol, dipropylene glycol, pentylene glycol, glycerin and any mixture thereof.

The aqueous phase can additionally comprise stabilizing agents such as sodium chloride, magnesium dichloride, magnesium sulphate, preferably sodium chloride.

Oxypropylenated and/or Oxyethylenated Polydimethyl(Methyl)Siloxane

According to a preferred embodiment, the composition according to the present invention comprises at least one oxypropylenated and/or oxyethylenated polydimethyl(methyl)siloxane as an emulsifier.

Use may be made, as oxypropylenated and/or oxyethylenated polydimethyl(methyl)siloxane, of those corresponding to the following formula (III):

(III)

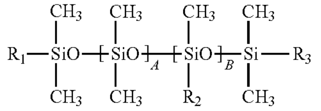

in which:

$R_1$, $R_2$ and $R_3$ represent, independently of one another, a $C_1$-$C_6$ alkyl radical or a $-(CH_2)_x-(OCH_2CH2)_y-(OCH_2CH_2CH_2)_z-OR_4$ radical, at least one $R_1$, $R_2$ or $R_3$ radical not being an alkyl radical; $R_4$ being a hydrogen, a $C_1$-$C_3$ alkyl radical or a $C_2$-$C_4$ acyl radical;

A is an integer ranging from 0 to 200;

B is an integer ranging from 0 to 50; provided that A and B are not equal to zero at the same time;

x is an integer ranging from 1 to 6;

y is an integer ranging from 1 to 30;

z is an integer ranging from 0 to 5.

According to a preferred embodiment of the present invention, in the compound of formula (III), $R_1$=$R_3$=methyl radical, x is an integer ranging from 2 to 6 and y is an integer ranging from 4 to 30, $R_4$ is in particular hydrogen.

Mention may be made, as examples of compounds of formula (II), of the compounds of formula (IV):

(IV)

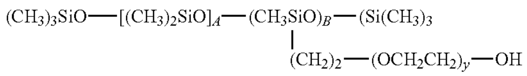

in which A is an integer ranging from 20 to 105, B is an integer ranging from 2 to 10 and y is an integer ranging from 5 to 20.

Mention may also be made, as examples of compounds of formula (II), of the compounds of formula (V):

$$HO-(CH_2CH_2O)_y-(CH_2)_3-[(CH_3)_2SiO]_{A'}-(CH_2)_3-(OCH_2CH_2)_y-OH \quad (V)$$

in which A' and y are integers ranging from 5 to 20, preferably from 8 to 20.

As Examples of oxypropylenated and/or oxyethylenated polydimethyl(methyl)siloxane, mention can be made to PEG-7 dimethicone, PEG-8 dimethicone, PEG-9 dimethicone, PEG-10 dimethicone, PEG-12 dimethicone, PEG-14 dimethicone, PEG-17 dimethicone and mixtures thereof.

Use may be made, as oxypropylenated and/or oxyethylenated polydimethyl(methyl)siloxane, of those sold under the names DC 5329, DC 7439-146, DC 2-5695 and Q4-3667 by Dow Corning; and KF-6013, KF-6015, KF-6016, KF-6017 and KF-6028 by Shin-Etsu.

In a preferred embodiment, the composition of the present invention comprises as oxypropylenated and/or oxyethylenated polydimethyl(methyl)siloxane one of those sold under the names KF-6013, KF-6015, KF-6016, KF-6017 and KF-6028 by Shin-Etsu, and more particularly KF-6017. The INCI name of KF-6017 is PEG-10 dimethicone.

Preferably, the composition according to the present invention may comprise the oxypropylenated and/or oxyethylenated polydimethyl(methyl)siloxane in an amount ranging from 0.1% to 2% by weight, preferably from 0.2% to 1.5% by weight, and preferentially from 0.5% to 1% by weight, relative to the total weight of the composition.

In a more preferred embodiment, the compositions of the present invention comprise PEG-10 dimethicone as oxypropylenated and/or oxyethylenated polydimethyl(methyl)siloxane, in an amount ranging from 0.1% to 2% by weight, preferably from 0.2% to 1.5% by weight, and more preferably from 0.5% to 1% by weight, relative to the total weight of the composition.

$C_8$-$C_{22}$ Alkyl Dimethicone Copolyol

According to a preferred embodiment, the composition of the present invention comprises at least one $C_8$-$C_{22}$ alkyl dimethicone copolyol as an emulsifier.

For the purpose of the present invention, $C_8$-$C_{22}$ alkyl dimethicone copolyol is different from oxypropylenated and/or oxyethylenated polydimethyl(methyl)siloxane as defined above.

Advantageously, the presence of $C_8$-$C_{22}$ alkyl dimethicone copolyol renders the compositions according to the present invention a good stability at ambient temperature (25° C.). The composition according to the present invention also exhibits a good stability at 37° C. or 45° C., in particular after storing for 2 months.

This $C_8$-$C_{22}$ alkyl dimethicone copolyol of the present invention is more particularly an oxypropylenated and/or oxyethylenated polymethyl ($C_8$-$C_{22}$) alkyl dimethyl methyl siloxane.

The $C_8$-$C_{22}$ alkyl dimethicone copolyol is advantageously a compound of the following formula (VI):

(VI)

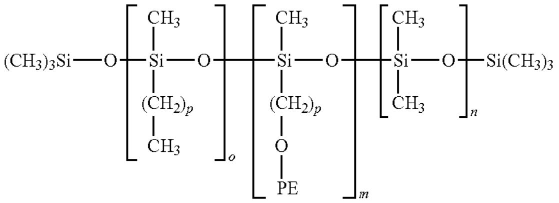

wherein:

PE represents from group $(-C_2H_4O)_x-(C_3H_6O)_y-R$, wherein R is selected from a hydrogen atom and an alkyl radical comprising from 1 to 4 carbon atoms, x is an integer ranging from 0 to 100, and y is an integer ranging from 0 to 80, provided that x and y are not simultaneously equal to 0; and m is an integer ranging from 1 to 40, n is an integer ranging from 10 to 200, o is an integer ranging from 1 to 100, p is an integer ranging from 7 to 21, and q is an integer ranging from 0 to 4.

Preferably, R is a hydrogen atom, m is an integer ranging from 1 to 10, n is an integer ranging from 10 to 100, o is an integer ranging from 1 to 30, p is 15, and q is 3.

In a preferred embodiment, the at least one $C_8$-$C_{22}$ alkyl dimethicone copolyol of the present invention is selected from cetyl dimethicone copolyols such as the product marketed under the name Abil EM-90 by the company Goldschmidt.

The composition according to the present invention may comprise $C_8$-$C_{22}$ alkyl dimethicone copolyol in an amount ranging from 0.1% to 1.5% by weight, preferably from 0.1% to 1% by weight, and more particularly from 0.1% to 0.8% by weight, relative to the total weight of the composition.

Abil EM-90 is a cetyl PEG/PPG-10/1 dimethicone.

In a more preferred embodiment, the composition of the present invention comprises cetyl PEG/PPG-10/1 dimethicone as $C_8$-$C_{22}$ alkyl dimethicone copolyol, in an amount ranging from 0.1% to 1.5% by weight, preferably from 0.2% to 1% by weight, and more particularly from 0.2% to 0.8% by weight, relative to the total weight of the composition.

In another preferred embodiment, the composition of the present invention comprises PEG-10 dimethicone as dimethicone copolyol, and cetyl PEG/PPG-10/1 dimethicone as $C_8$-$C_{22}$ alkyl dimethicone copolyol.

In another preferred embodiment, the composition of the present invention comprises from 0.5% to 1% by weight of PEG-10 dimethicone, and 0.2% to 0.8% by weight of cetyl PEG/PPG-10/1 dimethicone, relative to the total weight of the composition.

Active Ingredients

Optionally, the composition according to the present invention can further comprise active ingredients.

Mention may be made, as active ingredient which can be used in the composition of the present invention, for example, of moisturising agents, such as trehalose; vitamins, such as vitamin A (retinol), vitamin E (tocopherol), vitamin C (ascorbic acid), vitamin B5 (panthenol), vitamin B3 (niacinamide), the derivatives of these vitamins (in particular esters) and their mixtures; urea; caffeine; salicylic acid and its derivatives; alpha-hydroxy acids, such as lactic acid and glycolic acid, and their derivatives; retinoids, such as carotenoid and vitamin A derivatives; sunscreen; essential oils of mint, aloe vera or ginseng and their mixtures, emollients, such as hydrogenated polyisobutene, sensory adjusting agent, such as diphenyl dimethicone/vinyl diphenyl dimethicone/silsesquioxane crosspolymer.

In a preferred embodiment, the composition of the present invention can further comprise at least one active ingredient is ethyl menthane carboxamide.

In a preferred embodiment, the composition of the present invention can moreover comprise a chemical sunscreen such as any UV-A or UV-B screening agent which can be used in the cosmetics field. The sunscreens (or UV screening agents) can be selected from organic screening agents, physical screening agents and their mixtures, and can more particularly be selected from ethylhexyl methoxycinnamate, titanium dioxide or their mixture.

Additives

In a known way, the composition of the present invention can comprise one or more of the adjuvants usual in the cosmetic and dermatological fields: hydrophilic or lipophilic gelling and/or thickening agents, such as sodium hyaluronate and aluminum starch octenylsuccinate; fillers; sequestering agents; antioxidants; preservatives such as phenoxyethanol and chlorphenesin; basifying or acidifying agents; fragrances; emulsifiers, such as sorbitan sesquioleate and their mixtures.

The amounts of various adjuvants are those conventionally used in foundations.

Of course, a person skilled in the art will take care to choose the optional adjuvants added to the composition according to the present invention so that the advantageous properties intrinsically attached to the composition according to the present invention are not, or not substantially, detrimentally affected by the envisaged addition.

In a preferred embodiment, the present invention provides a solid cosmetic composition in form of a water-in-oil emulsion comprising, relative to the total weight of the composition:

(i) from 25 wt. % to 35 wt. % of at least one silicone oil selected from polydimethylsiloxane;

(ii) from 2 wt. % to 5 wt. % of ethylene homopolymer wax and from 2 wt. % to 5 wt. % of jojoba ester wax, both of them having a melt point having a melting point of greater than or equal to 65° C.;

(iii) at least 5 wt. % of pigment selected from mica, titanium oxides and iron oxides, untreated or coated with the disodium stearoylglutamate/aluminium hydroxide pairing, or a mixture thereof; and (iv) no less than 40 wt. % of an aqueous phase including at least one polyol selected from propylene glycol, dipropylene glycol, pentylene glycol, glycerin and any mixture thereof.

Galenic Form

The composition of the present invention is suitable to be used as a skin care, make up or cosmetic treatment product.

More particularly, the composition of the present invention is in the form of compact powder or cast solid product, for example, a stick foundation.

Method and Use

The composition according to the present invention can be used for caring for/making up the skin and particularly the face and/or neck.

The composition according to the present invention can be applied on the skin, with the fingers or an applicator by the users.

Thus, according to another aspect, the present invention provides a cosmetic method for caring and/or making up the skin, comprising application of a composition of the present invention on the skin.

Unless defined otherwise, all technical and scientific terms used herein have the same meaning as commonly understand by one of ordinary skill in the art to which the present invention pertains.

The examples that follow are given as non-limiting illustrations of the present invention.

EXAMPLES

Example 1

Stick Foundations in the form of water-in-oil emulsion of invention formula (Inv.1) and comparative formulas (Comp.) 1-2 were prepared (the contents are expressed as weight percentages of active material with regard to the total weight of each composition, unless otherwise indicated):

| Phase | INCI Name (trade name and supplier) | Inv.1 | Comp.1 Wt. % | Comp.2 |
|---|---|---|---|---|
| A1 | POLYETHYLENE(PERFORMALENE 500-L POLYETHYLENE from NEW PHASE TECHNOLOGIES) | 3.50 | — | 7.00 |
| | PARAFFIN (PARAFFINE PLASTIQUE 46/50 from AIGLON) | 2.00 | 2.00 | 2.00 |
| | JOJOBA ESTERS (JOJOBA ESTERS-70 from VANTAGE SPECIALTY CHEMICALS) | 3.50 | 7.00 | — |
| | CETYL PEG/PPG-10/1 DIMETHICONE (ABIL EM 90 from EVONIK GOLDSCHMIDT) | 0.43 | 0.43 | 0.43 |
| | PEG-10 DIMETHICONE (KF-6017 from SHIN ETSU) | 0.86 | 0.86 | 0.86 |
| | SORBITAN SESQUIOLEATE (SPAN 83-LQ-(MV) from CRODA) | 0.21 | 0.21 | 0.21 |
| | HYDROGENATED POLYISOBUTENE (PARLEAM from NOF CORPORATION) | 3.50 | 3.50 | 3.50 |
| | DIMETHICONE (KF-96L-2CS from SHIN ETSU) | QS 100 | QS 100 | QS 100 |
| A2 | DIMETHICONE (KF-96L-2CS from SHIN ETSU) | 4.50 | 4.50 | 4.50 |
| | TITANIUM DIOXIDE (and) DISODIUM STEAROYL GLUTAMATE (and) ALUMINUM HYDROXIDE (NAI-TAO-77891 from MIYOSHI KASEI) | 11.7 | 11.7 | 11.7 |
| | IRON OXIDES (and) DISODIUM STEAROYL GLUTAMATE (and) ALUMINUM HYDROXIDE (AMS YELLOW NO.602P from DAITO KASEI KOGYO) | 1.16 | 1.16 | 1.16 |
| | IRON OXIDES (and) DISODIUM STEAROYL GLUTAMATE (and) ALUMINUM HYDROXIDE (AMS RED NO.211P from DAITO KASEI KOGYO) | 0.36 | 0.36 | 0.36 |
| | IRON OXIDES (and) DISODIUM STEAROYL GLUTAMATE (and) ALUMINUM HYDROXIDE (AMS BLACK NO.710P from DAITO KASEI KOGYO) | 0.27 | 0.27 | 0.27 |
| A3 | DIPHENYL DIMETHICONE/VINYL DIPHENYL DIMETHICONE/SILSESQUIOXANE CROSSPOLYMER (KSP 300 from SHIN ETSU) | 1.00 | 1.00 | 1.00 |
| | MICA (and) TITANIUM DIOXIDE (TIMICA TERRA WHITE MN4501 from BASF) | 0.50 | 0.50 | 0.50 |
| | ALUMINUM STARCH OCTENYLSUCCINATE (DRY FLO PLUS from AKZO NOBEL) | 0.30 | 0.30 | 0.30 |
| A4 | DIMETHICONE(KF-96L-2CS from SHIN ETSU) | 3.00 | 3.00 | 3.00 |
| B | WATER | 38 | 38 | 38 |
| | PHENOXYETHANOL | 0.70 | 0.70 | 0.70 |
| | SODIUM CHLORIDE | 0.70 | 0.70 | 0.70 |
| | PENTYLENE GLYCOL | 1.50 | 1.50 | 1.50 |
| | CHLORPHENESIN | 0.30 | 0.30 | 0.30 |
| | SODIUM HYALURONATE | 0.02 | 0.02 | 0.02 |

The stick foundation of comparative formula does not comprise polyethylene wax with a melting point of greater than or equal to 65° C.

The stick foundation of comparative formula does not comprise jojoba ester wax with a melting point of greater than or equal to 65° C.

The stick foundations with formulas listed above were prepared according to the following steps:

1. Ingredients of A1 were added into a main beaker, heated to 90° C. and mixed until uniform;
2. Ingredients of A2 were ground until uniform and added into the main beaker, mixed for 5 minutes;
3. Ingredients of A3 were added into the main beaker and mixed for 5 minutes, then cooled to 80° C., thereto ingredients of A4 were added and mixed for 5 minutes;
4. Ingredients of B were premixed in a small beaker at 80° C. until uniform, and transferred into the main beaker and homogenized for 10 minutes at 80° C.

Example 2

The stability and hardness of the stick foundations of invention formula 1 and comparative formulas 1-2, and the spreadability and skin sensory upon application of them were evaluated.

The stability of each stick foundation was evaluated at 45° C., 37° C., and 4° C. for 8 weeks.

The hardness of each stick foundation was evaluated at room temperature with a TA-XT PLUS type texture analyzer from Stable Micro System as mentioned previously.

The spreadability of each stick foundation was evaluated with a MCR 301 type Rheometer from Anton Paar as follows.

A stick foundation to be tested was put on a plate and the value of shear stress at the cross point of G' (storage modulus) and G" (loss modulus) was measured with PP25 probe. The lower value means the better spreadability. Generally, a shear stress of no more than 500 Pa indicates good spreadability.

The skin sensory (including fresh and watery sensation) of each stick foundation was scored by 10 sensorial experts based on the following standard and averaged:

5: very good;
4: basically good;
3: acceptable;
2: slightly poor and not acceptable;
1: poor, not acceptable.

The results of stability, hardness, spreadability and skin sensory were summarized in the following table.

| | | Inv. 1 | Comp. 1 | Comp. 2 |
|---|---|---|---|---|
| stability | 45° C. | PASS | * | PASS |
| | 37° C. | PASS | * | PASS |
| | 4° C. | PASS | * | PASS |

-continued

| | Inv. 1 | Comp. 1 | Comp. 2 |
|---|---|---|---|
| Hardness (g) | 29.1 | 16.8 | 14.4 |
| Spreadability (Pa) | 162.9 | 15.7 | 59.2 |
| Skin sensory | 5 | 4 | 3 |

*not acceptable

It was observed that, the foundation of invention formula 1 was easily casted as a stick foundation, which enabled the consumers to use with either single hand or applicators for making up the skin. It was very convenient for the consumers to supplement the makeups of the skin during the day.

The invention claimed is:

1. A solid composition in the form of a water-in-oil emulsion comprising:

(i) at least one volatile silicone oil;

(ii) at least two waxes having a melting point of greater than or equal to 65° C. including polyethylene wax and jojoba ester wax;

(iii) at least 5 wt. % of a pigment, relative to the total weight of the composition, wherein the pigment is coated with a disodium stearoylglutamate/aluminum hydroxide pairing;

(iv) no less than 40 wt. % of an aqueous phase, relative to the total weight of the composition, (v) from 0.1 to 2.0% by weight of an oxypropylenated and/or oxyethylenated polydimethyl(methyl) siloxane of formula (III); and (vi) from 0.1 to 1.5% by weight of a ($C_8$-$C_{22}$) alkyl dimethicone copolyol of formula (VI):

(III)

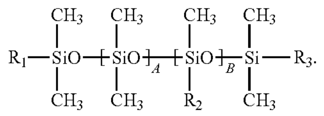

wherein $R_1$, $R_2$ and $R_3$ are each independently a $C_1$-$C_6$ alkyl radical or a $—(CH_2)_x—(OCH_2CH2)_y—(OCH_2CH_2CH_3)_z—OR_4$ radical, at least one $R_1$, $R_2$ or $R_3$ radical not being an alkyl radical; $R_4$ being a hydrogen, a $C_1$-$C_3$ alkyl radical or a $C_2$-$C_4$ acyl radical;

A is an integer from 0 to 200;

B is an integer from 0 to 50; provided that A and B are not equal to zero at the same time;

x is an integer from 1 to 6;

y is an integer from 1 to 30; and z is an integer from 0 to 5, (VI)

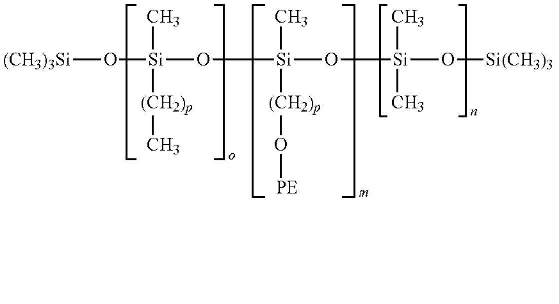

wherein:

PE is $(—C_2H_4O)_x—(C_3H_6O)_y—R$, wherein R is a hydrogen atom or an alkyl radical of from 1 to 4 carbon atoms, x is an integer from 0 to 100, and y is an integer from 0 to 80, provided that x and y are not simultaneously equal to 0; and m is an integer from 1 to 40, n is an integer from 10 to 200, o is an integer from 1 to 100, p is an integer from 7 to 21, and q is an integer from 0 to 4.

2. The solid composition according to claim 1, wherein the volatile silicone oil is selected from the group consisting of linear silicone oils, cyclic silicone oils, polymethylsiloxanes having alkyl, alkoxy or phenyl groups, which are pendent or at the end of a silicone chain, these groups having from 2 to 24 carbon atoms, and combinations thereof.

3. The solid composition according to claim 1, wherein the volatile silicone oil is present in the amount from 20 wt. % to 45 wt. %, relative to the total amount of the composition.

4. The solid composition according to claim 1, wherein the polyethylene wax is an ethylene homopolymer or a copolymer of ethylene and of another copolymerizable monomer corresponding to the following formula (I):

$$CH_2{=}CHR \qquad (I)$$

wherein

R represents a linear or branched alkyl chain which can be interrupted by mono- or polyoxyalkylene units, an aryl or aralkyl radical or $—CH_2COOH$ or $—CH_2CH_2OH$ radical.

5. The solid composition according to claim 1, wherein the polyethylene wax is present in the amount from 2 wt. % to 10 wt. % relative to the total amount of the composition.

6. The solid composition according to claim 1, wherein the jojoba ester wax is selected from fully hydrogenated jojoba ester of formula (II):

$$R^1—COO—CH_2—R^1 \qquad (II)$$

wherein $R^1$ is $CH_3—(CH_2)_y—$, and y is 16, 18, 20 or 22.

7. The solid composition according to claim 1, wherein the jojoba ester wax is present in the amount from 1 wt. % to 10 wt. % relative to the total amount of the composition.

8. The solid composition according to claim 1, wherein the pigment is selected from the group consisting of an oxide of titanium, an oxide of zirconium, an oxide of cerium, an oxide of zinc, an oxide of iron, an oxide of chromium, a dioxide of titanium, a dioxide of zirconium, a dioxide of cerium, mica, Prussian blue, manganese violet, ultramarine blue, chromium hydrate, and mixtures thereof.

9. The solid composition according to claim 1, wherein the pigment is present in the amount up to 18 wt. %, relative to the total weight of the composition.

10. The solid composition according to claim 1, wherein the aqueous phase further comprises at least one polyol selected from the group consisting of propylene glycol, dipropylene glycol, pentylene glycol, glycerin and any mixture thereof.

11. The solid composition according to claim 1 comprising, relative to the total weight of the composition:

(i) from 25 wt. % to 35 wt. % of at least one volatile polydimethylsiloxane oil;

(ii) from 2 wt. % to 5 wt. % of ethylene homopolymer wax and from 2 wt. % to 5 wt. % of jojoba ester wax, both of which having a melt point of greater than or equal to 65° C.;

(iii) at least 5 wt. % of pigment selected from the group consisting of mica, titanium oxides and iron oxides, coated with a disodium stearoylglutamate/aluminium hydroxide pairing, or a mixture thereof coated with a disodium stearoylglutamate/aluminium hydroxide pairing; and (iv) no less than 40 wt. % of an aqueous phase including at least one polyol selected from the group consisting of propylene glycol, dipropylene glycol, pentylene glycol, glycerin and any mixture thereof.

12. The solid composition according to claim 1, wherein $R_1=R_3$=methyl radical, x is an integer from 2 to 6 and y is an integer from 4 to 30.

13. The solid composition according to claim 1, wherein the ($C_8$-$C_{22}$) alkyl dimethicone copolyol is cetyl PEG/PPG-10/1 dimethicone.

14. A cosmetic method for caring for and/or making up the skin, comprising the application of a composition according to claim 1 on the skin.

* * * * *